United States Patent [19]
Manoukian

[11] Patent Number: 5,395,360
[45] Date of Patent: Mar. 7, 1995

[54] DAMAGE RESISTANT STERILIZABLE FIBER OPTIC PROBE ASSEMBLY

[75] Inventor: Nubar Manoukian, Cupertino, Calif.

[73] Assignee: Coherent, Inc., Santa Clara, Calif.

[21] Appl. No.: 200,223

[22] Filed: Feb. 23, 1994

[51] Int. Cl.⁶ ............................................. A61B 17/36
[52] U.S. Cl. ........................................ 606/15; 606/1; 604/199
[58] Field of Search ................ 606/1, 15, 16; 604/199

[56] References Cited

U.S. PATENT DOCUMENTS

| | | | |
|---|---|---|---|
| 2,677,374 | 5/1954 | Burnside | 604/199 |
| 3,754,644 | 8/1973 | Hampel | 604/199 X |
| 4,538,609 | 9/1985 | Takenaka et al. | 606/16 |
| 5,125,058 | 6/1992 | Tenerz et al. | 606/16 X |
| 5,267,996 | 12/1993 | Fletcher | 606/16 X |
| 5,304,172 | 4/1994 | Manoukian | 606/16 X |

*Primary Examiner*—Peter A. Aschenbrenner
*Attorney, Agent, or Firm*—Limbach & Limbach

[57] ABSTRACT

An approach for sterilizing and reusing a fiber optic probe is disclosed. The fiber optic probe includes an input end having an axially projecting stem containing the input face of the fiber. Prior to sterilization, a cap member is mounted on the stem to prevent damage by the pressurized steam encountered in an autoclave. After being sterilized, the probe is brought to the operating theater. The sterilized probe is transferred to the sterile field while the stem and cap member are extended beyond the sterile field. The cap member is then removed and the input end of the probe is connected to the source of laser radiation. Using this approach, the probe can be sterilized without damage and reused without contaminating the sterile field.

15 Claims, 2 Drawing Sheets

DAMAGE RESISTANT STERILIZABLE FIBER OPTIC PROBE ASSEMBLY

TECHNICAL FIELD

The subject invention relates to a fiber optic probe used for delivering high powered laser radiation to a treatment site during surgical procedures.

BACKGROUND OF THE INVENTION

In recent years, lasers have been employed in a wide variety of surgical procedures. For certain laser wavelengths, silica based optical fibers are suitable for delivering the laser energy from the source to the treatment site. Much effort has been expended in developing fiber optic probes for use in various types of surgeries.

Initial development efforts by the assignee herein were directed to designing a probe which could survive in the harsh environment created when high energy laser pulses are used to ablate relatively hard tissue such as cartilage and bone. More specifically, when the probe is used to deliver high energy pulses (e.g. in excess of one joule per pulse), the delivery end of the probe is subjected to heat and debris generated at the treatment site which can destroy the probe. Various design approaches have been developed to minimize damage to the delivery end of the probe during the treatment procedure. Details of the types of structures intended to prevent damage to the delivery end of the probe during a surgical procedure can be found in U.S. Pat. No. 5,257,989, issued Nov. 2, 1993, and U.S. Ser. No. 905,125, filed Jun. 23, 1992, both of which are assigned to the same assignee herein and incorporated by reference.

The designs described in the above cited references have been so successful in minimizing damage to the delivery end of the probe that it became possible to contemplate reusing the probes in second and subsequent surgical procedures. Of course, prior to reusing a probe with another patient, the probe needs to be sterilized. Therefore, additional efforts were made to design a probe which could be repeatedly sterilized. Such a probe must be able to withstand the high pressure, high temperature steam encountered in an autoclave.

To achieve this goal, the materials forming the probe were carefully selected. In addition, the internal structure of the probe was designed to remain stable during temperature cycling encountered in an autoclave. Details of this improved design are set forth in U.S. patent application Ser. No. 08/016,768, filed Feb. 11, 1993, assigned to the same assignee herein and incorporated by reference.

By using the design approaches described in the above cited references, probes were developed that could be sterilized and reused a number of times. However, even with the developments described above, a small percentage of fibers experienced failure upon reuse. The observed failure mechanism included overheating of the coupler connecting the probe to the laser device which can lead to catastrophic damage.

Various efforts were made to diagnosis and address this problem. In the belief that damage was occurring to the input face of the fiber, this input face was polished to increase its strength. While polishing the input face of the fiber resulted in a noticeable reduction in the observed failure rate, the subject invention disclosed below was developed to essentially eliminate these failures.

While studying the failure mechanism described above, the inventor herein discovered that the exposure of the input face of the fiber to the cycling of the pressurized steam occurring during sterilization in the autoclave enhanced and accelerated the formation of cracks in the silica glass at the fiber surface. It had been previously reported that water molecules in the presence of cracks in glass can accelerate the breakdown of bonds. (See, "The Fracturing of Glass," Michalske and Bunker, *Scientific American,* December, 1987, pages 122-129.) As can be appreciated, the high pressures generated in an autoclave can force steam molecules into any microscopic cracks present in the fiber, accelerating the break down of atomic bonds. It is also believed that when the autoclave is rapidly depressurized, turbulence is created forcing debris into the input face of the fiber thereby increasing the damage. These cracks and other imperfections lead to breakdown of the fiber during use.

When the fiber optic probe is used in a surgical procedure, the input coupler is connected to the operating laser source such that the output of the laser source is focused onto the input face of the fiber. Typically, the diameter of the focal spot on the input face is about one-half the size of the diameter of the fiber to insure that all the light energy from the laser is coupled into the fiber. Due to this concentrated focusing of the input light, the power density on the input face is quite high. If microcracks are present in the input face, a portion of the light is scattered, causing heating and then melting of the fiber which sharply decreases the amount of light being coupled into the fiber. At this point, the scattered light will heat and burn the coupler and the probe will have to replaced.

This type of failure mechanism is not observed at the delivery end of the probe in the present designs. It is believed that the overheating problem is less acute since the power density at the delivery end is much lower than at the input face. The power density is much lower at the delivery end because as the beam propagates along the fiber, it expands such that by the time it exits the fiber, the beam diameter will match the diameter of the fiber.

Accordingly, it was desirable to develop an approach which would minimize the damage to the input face of the fiber while still allowing the probe to be sterilized.

SUMMARY OF THE INVENTION

This and other objects were achieved by the assembly and method of the subject invention. More specifically, in accordance with the subject invention, a protective cap member was designed to cover the input end of the probe thereby isolating the input face of the fiber from the pressurized steam in the autoclave. In the design of the assignee's current fiber optic probes, the input end includes an axially extending stem containing the input face of the fiber. This stem is received in a mating female connector on the laser device. The protective cap member is designed to fit over this stem.

In accordance with the subject invention, the protective cap member is formed from a resilient material and has a open channel which is sealed at one end. The relaxed diameter of the channel is less than the diameter of the stem. In use, the cap member is forced over the stem creating a hermetic seal surrounding the input face of the fiber. The composite assembly is then sterilized in the autoclave. When removed, both the probe and protective cap are in a sterile condition. However, the stem, which has been isolated from the pressurized steam is not sterile.

Therefore, in accordance with the method of the subject invention, the composite assembly (which is typically held in a sterile support tray) is supplied to the sterile field in the surgical theater. The assembly is then opened and the input end including the stem and protective cap member is passed out of the sterile field where the laser is located. At this time, the circulating nurse can remove the cap member from the stem and connect the input end of the probe to the laser. In this manner, the unsterilized stem will not be exposed to the sterile field. In addition, the input face of the fiber will have been isolated from the harsh environment of the autoclave. In experimental testing, it has been found that the subject method essentially eliminates the previously observed failure mode allowing the probe to be reused safely ten or more times.

Further objects and advantages of the subject invention will become apparent from the following detailed description taken in conjunction with the drawings in which:

DETAILED DESCRIPTION OF THE PREFERRED EMBODIMENT

Figure 1:
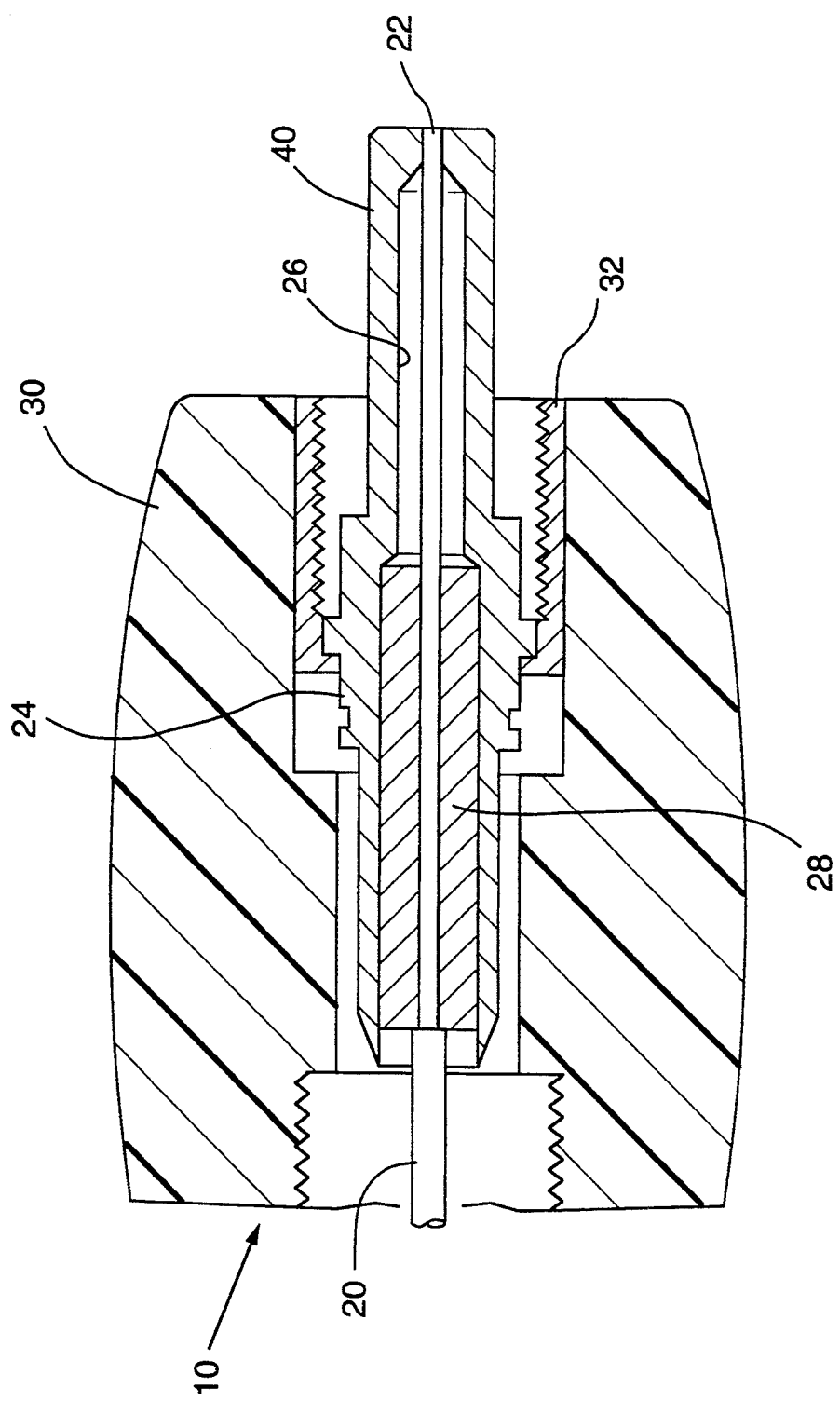
FIG. 1 is a cross sectional view of the input end of a fiber optic probe.

Referring to FIG. 1, there is shown a partial view of the input end of a fiber optic probe 10. More details of the structure of the entire probe can be obtained from the references cited above. The input end of the probe 10 is configured to be connected to a laser source (not shown). Light from the laser source is coupled to the probe and transmitted by an internal fiber 20, from the input face 22 to the delivery end (not shown).

The input end of the probe includes a conventional SMA connector 24 formed from metal and including a central channel 26. The input end of the fiber is supported within connector 24 via a collet 28. Connector 24 is surrounded by a coupling nut 30 formed from a hard plastic. Nut 30 supports a threaded ring 32 for connection to the laser source. The rear end of the coupler 34 is formed from a more pliable material such a silicone. The free end of the connector 24 terminates in an axially extending stem 40. While the use of an SMA connector with an axially extending stem 40 is relatively standard in the industry, other configurations are possible. It is believed the subject invention could be adapted for use with other designs as well.

Figure 2:
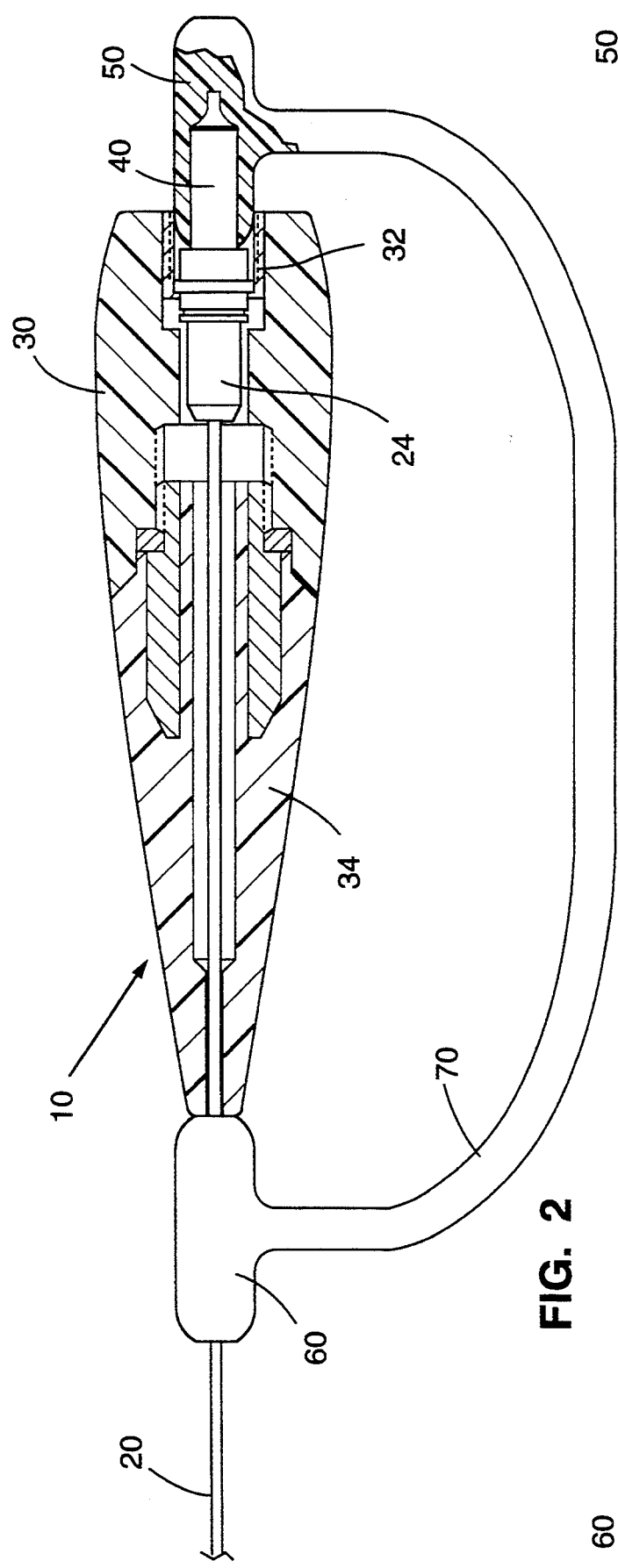
FIG. 2 is a side elevational view, partially in section, of the input end of a fiber optic probe showing the protective cap member of the subject invention sealably mounted to the stem of the probe.

As noted above, the applicant herein has discovered that the environment encountered in a steam autoclave can cause significant damage to the input face 22 of the fiber. Accordingly, a new approach was developed which functions to protect the input face of the fiber while still being able to sterilize the remainder of the probe and thereafter reuse the probe without contaminating the sterile field. In accordance with the subject invention, prior to placing the probe 10 in an autoclave for sterilization, the input face of the fiber is sealed with a protective cap member 50 as illustrated in FIG. 2.

Figure 3:
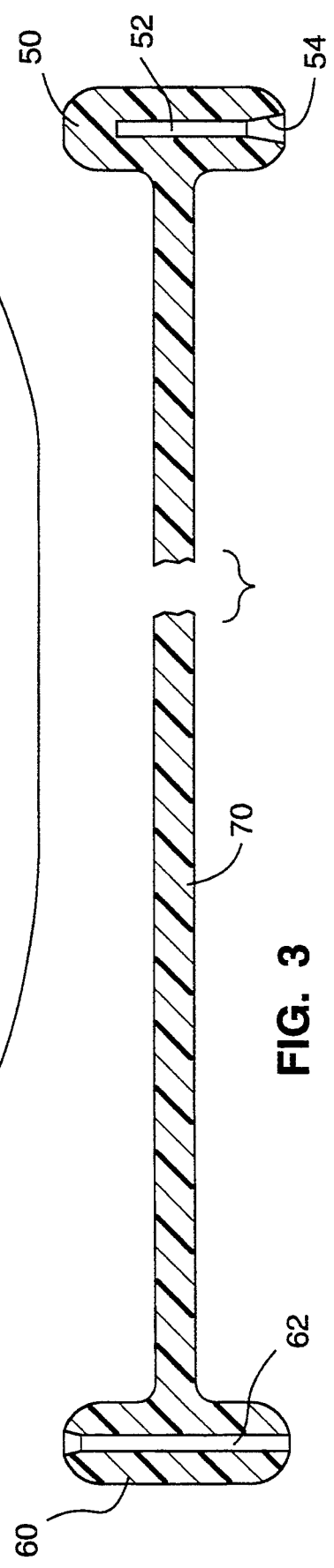
FIG. 3 is a cross sectional view of the protective cap member, support member and strap of the subject invention.

In the preferred embodiment, cap member 50 is formed from a pliable material such as silicone. As best seen in FIG. 3, the cap member includes a central channel 52, partially extending along the length thereof. Channel 52 includes a conically shaped entrance 54 leading to a narrow, central bore. Preferably, the relaxed diameter of the bore is less than the diameter of the stem. In the present commercial embodiment, the diameter of the stem 40 is on the order of 0.125 inches. In this case, the relaxed diameter of the main bore of the channel 52 can be 0.050 inches. The axial length of the channel is on the order of 0.55 inches.

Prior to placing the probe in the autoclave, the resilient cap 50 is twisted onto the stem. The conical entrance 54 will facilitate alignment and insertion of the stem within the channel. Since the diameter of the stem is larger than the diameter of the channel, as the stem is forced into the channel, the diameter of the channel will expand. However, the resilient nature of the cap member will help maintain a snug fit between the cap member and the stem. It is also believed that the pressure developed in the autoclave will place an external compression force on the cap member further enhancing the seal. It is intended that the cap member insure that virtually no water vapor reaches the input face of the fiber. Preferably, the front end of the cap will abut the inner diameter of ring 32 to further enhance the seal.

Once the cap member is installed and the probe assembly is placed in the autoclave, the sterilization procedure can begin. This procedure includes raising the temperature and pressure of the steam in the autoclave chamber. After a predetermined interval, the chamber is cooled and depressurized. The probe can then be removed. In current practice, the probe is fitted within a support tray during the sterilization procedure. Both the probe and the support tray are sterilized. In the accordance with the subject invention, the outer surface of the cap member is sterilized as well.

After sterilization, the probe can be used or stored in the tray until needed. At the start of a procedure, the tray is brought into the sterile field in the operating theater. A nurse in the sterile field will unpack the probe, uncoiling the fiber. The input end, covered by the sterile cap member, is then handed to a circulating nurse outside the sterile field. At this time, the circulating nurse can remove the cap member exposing the non-sterile stem and fiber input face. The input end of the probe is then connected to the laser source which is also located outside the sterile field.

As can be appreciated, the approach described above allows the input face of the fiber to be protected during sterilization yet permits the safe use of the probe, which includes an unsterile stem, in the sterile field. This approach has substantially eliminated the prior failure mechanisms allowing the probe to be reused many times.

Since the protective cap member 50 is relatively small and should be reused during each subsequent sterilization procedure, it is preferable to provide a means for preventing the loss of the cap member. In accordance with the subject invention, this goal is achieved by forming a support member 60 with an inner channel 62 for mounting about the fiber at a point spaced from the input face thereof. In the preferred embodiment, the support member 60 is formed from the same material as the cap member 50 and is mounted during assembly of the probe. A resilient strap 70 interconnects the cap member 50 with the support member 60. When the cap member is removed from the stem to connect the probe to the laser, the cap member will hang from the strap. When the surgical procedure is finished and the probe is disconnected from the laser, the cap member can be remounted on the stem to protect the input face 22 of the fiber from the environment.

While the subject invention has been described with reference to a preferred embodiment, various changes and modifications could be made therein, by one skilled in the art, without varying from the scope and spirit of the subject invention as defined by the appended claims.

I claim:

1. A damage resistant assembly capable of being sterilized in a steam autoclave comprising:
   a fiber optic probe, said probe including an elongated optical fiber, said probe having an input end connectable to a source of laser radiation and a delivery end for emitting the laser radiation, said input end terminating in an axially projecting stem supporting the input face of the optical fiber; and
   a removable cap member sealably mounted over said stem at the input end of the probe and isolating said input face of the optical fiber from pressurized steam encountered in an autoclave.

2. An assembly as recited in claim 1 wherein said cap member is formed from a resilient material and includes an open channel for receiving said stem, said channel partially extending through the cap member, said channel having a relaxed diameter less than the diameter of the stem so that when the cap member is mounted on said stem, a water-tight seal is created.

3. An assembly as recited in claim 2 wherein the open end of the channel is defined by a conical configuration.

4. An assembly as recited in claim 2 wherein said cap member is formed from silicone.

5. An assembly as recited in claim 2 wherein said cap member further includes a separate means for connecting the cap member to the probe when the cap member is removed from the stem.

6. An assembly as recited in claim 5 further including a support member connected to the optical fiber at a point spaced from the input end thereof, said assembly further including a flexible strap interconnecting the support member and the cap member.

7. An assembly as recited in claim 6 wherein said support member includes a central channel so that said support member can be mounted about the optical fiber.

8. A method of reusing a fiber optic probe, said probe including an elongated optical fiber, said probe having an input end connectable to a source of laser radiation and a delivery end for emitting the laser radiation, said input end supporting the input face of the optical fiber, said method comprising the steps of:
   placing a cap member on the input end of the probe in a manner to seal the input face of the optical fiber;
   placing the probe and cap member in an autoclave;
   sterilizing the outer surface of the probe and cap member using pressurized steam;
   removing the sterilized probe from the autoclave;
   transferring the sterilized probe to the sterile field in a surgical theater while the stem and cap member are extended beyond the sterile field;
   removing the cap member from the input end of the probe; and
   connecting the input end of the probe to the source of laser radiation.

9. A method as recited in claim 8 wherein the input end of the probe terminates in an axially projecting stem containing the input face of the optical fiber and wherein said cap member is placed over said stem.

10. A method as recited in claim 9 wherein the cap member is formed from a resilient material and includes an open channel for receiving said stem, said channel partially extending through the cap member, said channel having a relaxed diameter less than the diameter of the stem so that during the step of placing the cap member on the stem, the stem expands the channel and creates a water-tight seal.

11. A method as recited in claim 10 wherein the open end of the channel is defined by a conical configuration.

12. A method as recited in claim 10 wherein said cap member is formed from silicone.

13. A method as recited in claim 10 wherein said cap member further includes a separate means for connecting the cap member to the probe when the cap member is removed from the stem.

14. A method as recited in claim 13 further including a support member connected to the optical fiber at a point spaced from the input end thereof, said assembly further including a flexible strap interconnecting the support member and the cap member.

15. A method as recited in claim 14 wherein said support member includes a central channel so that said support member can be mounted about the optical fiber.

* * * * *